United States Patent
Demaria et al.

(10) Patent No.: US 11,045,601 B2
(45) Date of Patent: Jun. 29, 2021

(54) INFUSION SET WITH COMPONENTS COMPRISING A POLYMERIC SORBENT TO REDUCE THE CONCENTRATION OF M-CRESOL IN INSULIN

(71) Applicant: Eli Lilly and Company, Indianapolis, IN (US)

(72) Inventors: Christopher John Demaria, Stow, MA (US); Daniel Morris Hartmann, Arlington, MA (US); Graham Barry Jones, South Easton, MA (US); Christopher Kovalchick, Bedford, MA (US); Sean Matthew Pszenny, Cambridge, MA (US); Rhea Sirkar, Brighton, MA (US); Monica Rixman Swinney, Stoneham, MA (US)

(73) Assignee: Eli Lilly and Company, Indianapolis, IN (US)

( * ) Notice: Subject to any disclaimer, the term of this patent is extended or adjusted under 35 U.S.C. 154(b) by 357 days.

(21) Appl. No.: 16/094,628

(22) PCT Filed: Apr. 21, 2017

(86) PCT No.: PCT/US2017/028850
§ 371 (c)(1),
(2) Date: Oct. 18, 2018

(87) PCT Pub. No.: WO2017/184985
PCT Pub. Date: Oct. 26, 2017

(65) Prior Publication Data
US 2019/0054233 A1 Feb. 21, 2019

Related U.S. Application Data

(60) Provisional application No. 62/326,257, filed on Apr. 22, 2016.

(51) Int. Cl.
*A61M 5/165* (2006.01)
*A61M 5/142* (2006.01)
(Continued)

(52) U.S. Cl.
CPC ............ *A61M 5/165* (2013.01); *A61K 38/28* (2013.01); *A61M 5/14248* (2013.01);
(Continued)

(58) Field of Classification Search
CPC ............ A61M 5/165; A61M 5/14248; A61M 2005/1657; A61K 47/50; A61K 38/28
See application file for complete search history.

(56) References Cited

U.S. PATENT DOCUMENTS

| 2,748,769 A | 6/1956 | Huber |
| 3,076,457 A | 2/1963 | Copen |

(Continued)

FOREIGN PATENT DOCUMENTS

| EP | 0956155 | 8/2002 |
| WO | 02/094352 | 11/2002 |

(Continued)

OTHER PUBLICATIONS

International Search Report of the International Searching Authority pertaining to International Application No. PCT/US2017/028850; dated Aug. 21, 2017; 6 pages.

(Continued)

*Primary Examiner* — Nathan R Price
*Assistant Examiner* — Melissa A Snyder
(74) *Attorney, Agent, or Firm* — Jonathan Anderson

(57) ABSTRACT

An insulin infusion set (IIS) device with one or more features designed to achieve longevity in a patients continuous subcutaneous insulin infusion (CSII) site viability. One exemplary feature is an adsorbent material configured to adsorb phenolic excipients (e.g., m-cresol or other preser- (Continued)

vatives) from the insulin formulation. The adsorbent material may be positioned along a fluid pathway specifically designed to increase and/or extend exposure between the insulin formulation and the adsorbent material. Another exemplary feature is a medicament configured to reduce the patients inflammation or slow the progression of the patients inflammatory response. Yet another exemplary feature is a diffusive catheter configured to deliver the insulin formulation in a diffuse manner.

22 Claims, 11 Drawing Sheets

(51) Int. Cl.
    *B01J 20/26*     (2006.01)
    *C07K 14/62*     (2006.01)
    *A61K 38/28*     (2006.01)
    *C07K 1/34*     (2006.01)
    *A61M 5/158*     (2006.01)

(52) U.S. Cl.
    CPC ........... *B01J 20/262* (2013.01); *B01J 20/264* (2013.01); *C07K 14/62* (2013.01); *A61M 2005/1581* (2013.01); *A61M 2005/1587* (2013.01); *A61M 2202/07* (2013.01); *B01J 2220/64* (2013.01); *C07K 1/34* (2013.01)

(56) References Cited

U.S. PATENT DOCUMENTS

| | | | |
|---|---|---|---|
| 3,812,031 A | | 5/1974 | McCoy et al. |
| 4,411,795 A | * | 10/1983 | Olson ............... A61L 2/0082 210/679 |
| 4,413,993 A | | 11/1983 | Guttman |
| 4,592,920 A | | 6/1986 | Murtfeldt |
| 4,790,830 A | | 12/1988 | Hamacher |
| 4,838,877 A | | 6/1989 | Massau |
| 4,976,703 A | | 12/1990 | Franetzki et al. |
| 5,108,617 A | * | 4/1992 | Eriksson ............ B01J 20/183 210/679 |
| 5,505,713 A | | 4/1996 | Van Antwerp |
| 5,567,495 A | | 10/1996 | Modak et al. |
| 5,569,463 A | | 10/1996 | Helmus et al. |
| 5,599,321 A | | 2/1997 | Conway et al. |
| 5,702,372 A | | 12/1997 | Nelson |
| 5,936,061 A | * | 8/1999 | Andersson ............ B01D 15/00 210/679 |
| 6,110,155 A | * | 8/2000 | Baudino ............... A61L 29/08 604/264 |
| 6,110,483 A | | 8/2000 | Whitbourne et al. |
| 6,241,710 B1 | | 6/2001 | VanTassel et al. |
| 6,261,272 B1 | | 7/2001 | Gross et al. |
| 6,302,990 B1 | | 10/2001 | Nelson |
| 6,366,794 B1 | | 4/2002 | Moussy et al. |
| 6,443,942 B2 | | 9/2002 | Van Antwerp et al. |
| 6,475,196 B1 | | 11/2002 | Vachon |
| 6,589,224 B2 | * | 7/2003 | Winchester ........... A61M 5/165 604/126 |
| 7,153,265 B2 | | 12/2006 | Vachon |
| 7,157,528 B2 | | 1/2007 | Ward |
| 7,875,008 B2 | | 1/2011 | Chong et al. |
| 7,883,488 B2 | | 2/2011 | Shantha et al. |
| 7,914,504 B2 | | 3/2011 | Klein |
| 8,012,192 B2 | | 9/2011 | Eidenschink et al. |
| 8,372,423 B2 | | 2/2013 | Marshall et al. |
| 8,512,731 B2 | | 8/2013 | Yang et al. |
| 8,609,642 B2 | | 12/2013 | Whitbourne |
| 8,802,603 B2 | | 8/2014 | D'Souza et al. |
| 9,220,837 B2 | | 12/2015 | Pesach et al. |
| 2002/0156434 A1 | | 10/2002 | Van Antwerp et al. |
| 2003/0208166 A1 | | 11/2003 | Schwartz |
| 2005/0148928 A1 | | 7/2005 | Molina et al. |
| 2005/0203000 A1 | | 9/2005 | Sutter et al. |
| 2007/0197957 A1 | | 8/2007 | Hunter et al. |
| 2007/0299409 A1 | | 12/2007 | Whitbourne et al. |
| 2008/0311321 A1 | | 12/2008 | Sparholt et al. |
| 2009/0252699 A1 | | 10/2009 | Kocher et al. |
| 2010/0010413 A1 | | 1/2010 | Loiterman |
| 2011/0152820 A1 | | 6/2011 | Chattaraj et al. |
| 2011/0313391 A1 | | 12/2011 | Knapp, II et al. |
| 2012/0265166 A1 | | 10/2012 | Yodfat |
| 2013/0029606 A1 | | 1/2013 | Wang et al. |
| 2014/0100522 A1 | | 4/2014 | Nie et al. |
| 2014/0107593 A1 | | 4/2014 | Gao et al. |
| 2014/0378891 A1 | * | 12/2014 | Searle etal. ........... A61M 5/152 604/22 |
| 2015/0045718 A1 | | 2/2015 | Shlomo et al. |
| 2015/0051583 A1 | | 2/2015 | Horvath et al. |
| 2015/0112302 A1 | | 4/2015 | Chattaraj et al. |
| 2015/0328370 A1 | | 11/2015 | Petisce et al. |
| 2016/0074560 A1 | | 3/2016 | Rosenblatt et al. |
| 2016/0354542 A1 | | 12/2016 | Ward et al. |

FOREIGN PATENT DOCUMENTS

| | | |
|---|---|---|
| WO | 2003020336 | 3/2003 |
| WO | 2004/024219 | 3/2004 |
| WO | 2006015600 | 2/2006 |
| WO | 2009027478 | 3/2009 |
| WO | 2016196516 | 12/2016 |

OTHER PUBLICATIONS

Written Opinion of the International Searching Authority pertaining to International Application No. PCT/US2017/028850; dated Aug. 21, 2017; 14 pages.
Morais, J. M., Papadimitrakopoulos, F., & Burgess, D. J. (2010). Biomaterials/Tissue Interactions: Possible Solutions to Overcome Foreign Body Response. *The AAPS journal*, 12(2), 188-196.
Singh, S. M., Hutchings, R. L., & Mallela, K. M. (2011). "Mechanisms of m-cresol-induced protein aggregation studied using a model protein cytochrome c". *Journal of pharmaceutical sciences*, 100(5), 1679-1689.
Hutchings, R. L., Singh, S. M., Cabello-Villegas, J., & Mallela, K. M. (2013). "Effect of antimicrobial preservatives on partial protein unfolding and aggregation". *Journal of pharmaceutical sciences*, 102(2), 365-376.
Krishnan, M. R., Samitsu, S., Fujii, Y., & Ichinose, I. (2014). "Hydrophilic Polymer Nanofibre Networks for Rapid Removal of Aromatic Compounds from Water". *Chemical Communications*, 50(66), 9393-9396.
Bis, R. L., & Mallela, K. M. (2014). "Antimicrobial preservatives induce aggregation of interferon alpha-2a: The order in which preservatives induce protein aggregation is independent of the protein". *International journal of pharmaceutics*, 472(1-2), 356-361.
Weber, C., Kammerer, D., Streit, B., & Licht, A. H. (2015). "Phenolic Excipients of Insulin Formulations Induce Cell Death, Pro-Inflammatory Signaling and MCP-1 Release". *Toxicology reports*, 2, 194-202.
Paiva, T. O., Bastos, A. E. P., Marquês, J. T., Viana, A. S., Lima, P. A., & de Almeida, R. F. M. (2016). "m-Cresol affects the lipid bilayer in membrane models and living neurons". *RSC Advances*, 6(107), 105699-105712.
Woodley, W.D., et al., In Vivo Model for Fluoroscopic Imaging of Large Volume Injections at a Range of Viscosities and Flow Rates, poster presented at the Parenteral Drug Association (PDA) Annual Meeting, San Antonio, TX, Mar. 14-16, 2016.

\* cited by examiner

INFUSION SET WITH COMPONENTS COMPRISING A POLYMERIC SORBENT TO REDUCE THE CONCENTRATION OF M-CRESOL IN INSULIN

CROSS REFERENCE TO RELATED APPLICATION

This application is a National Stage of International Application No. PCT/US2017/028850, filed Apr. 21, 2017, which claims priority to U.S. Provisional Patent Application Ser. No. 62/326,257, filed Apr. 22, 2016, the disclosures of which are hereby expressly incorporated by reference herein in their entirety.

FIELD OF THE DISCLOSURE

The present disclosure relates to a device for parenteral drug delivery, more specifically a device for continuous subcutaneous insulin infusion (CSII).

BACKGROUND OF THE DISCLOSURE

CSII may be performed using an insulin infusion set (IIS). One example of an IIS device 100 is shown in FIG. 1. The illustrative device 100 includes a first, proximal end 112 that communicates with an insulin reservoir of a pump (not shown) to receive an insulin formulation and a second, distal end 114 that communicates with a patient (not shown) to deliver the insulin formulation (i.e., the infusate). At the first end 112, the illustrative device 100 includes a reservoir connector 120 configured to couple with the insulin reservoir, a line set tubing 122, and a base connector 124. At the second end 114, the illustrative device 100 includes an infusion base 130 configured to receive the base connector 124, an adhesive pad 132 configured to adhere the infusion base 130 to the patient's skin, and an infusion catheter 134 configured for insertion into the patient's skin. In use, the insulin formulation is directed from the pump, through the line set tubing 122, through the infusion catheter 134, and into the patient's subcutaneous (SC) tissue.

IIS devices may vary in size, shape, appearance, materials, and other features. In one example, the material used to construct the infusion catheter 134 may vary (e.g., the Contact Detach™ Infusion Set available from Animas Corporation uses a steel infusion catheter, whereas the MiniMed® Quick-set® Infusion Set available from Medtronic uses a plastic infusion catheter). In another example, the arrangement of line set tubing 122 may vary (e.g., the Contact Detach™ Infusion Set available from Animas Corporation uses two sets of a line set tubing coupled together via an intermediate strain-relief base, whereas the MiniMed® Quick-set® Infusion Set available from Medtronic uses a single line set tubing).

The patient's body may exhibit an inflammatory and/or foreign body response at the site of the infusion catheter 134. This response at the infusion site may vary from patient to patient depending on various factors, including the patient's susceptibility to wound formation, the patient's associated tissue remodeling and the patient's sensitivity to the particular insulin formulation, including phenolic excipients (e.g., m-cresol, phenol, methylparaben, ethylparaben, butylbaraben, other preservatives, and combinations thereof) in the insulin formulation, for example. M-cresol, in particular, has been shown to induce inflammatory pathways [Weber, 2015], negatively impact human immune cell types in vitro [Woodley, 2016], degrade lipid bilayers and neuronal cell membranes [Paiva, 2013], and induce aggregation of proteins and initiate protein unfolding which might contribute to infusion site events [Bis, 2015; Singh, 2011; Hutchings, 2013].

Due to these inflammatory and/or foreign body responses at the infusion sites, known IIS devices for CSII are currently indicated for two- to three-day (2-3 d) use. After even a short wear time, the inflammatory and/or foreign body response may impair the efficacy of the patient's infusion site, thereby limiting insulin uptake, increasing the risk of hyperglycemia, and limiting viable infusion site longevity. The limited wear time for IIS devices represents a two- to seven-times discrepancy compared with the wear time for continuous glucose monitors (CGMs), thus introducing an obstacle to achieving a convenient, fully integrated CSII/CGM artificial pancreas system.

SUMMARY

The present disclosure provides an IIS device with one or more features designed to achieve longevity in a patient's CSII infusion site viability. One exemplary feature is a sorbent material configured to collect phenolic excipients m-cresol, phenol, methylparaben, ethylparaben, butylbaraben, other preservatives, and combinations thereof) from the insulin formulation by sorption, such as adsorption and/or absorption. The sorbent material may be positioned along a fluid pathway specifically designed to increase and/or extend exposure between the insulin formulation and the sorbent material. Another exemplary feature is a medicament configured to reduce the patient's inflammation or slow the progression of the patient's inflammatory response. Yet another exemplary feature is a diffusive catheter configured to deliver the insulin formulation to the patient in a diffuse manner.

According to an embodiment of the present disclosure, an insulin infusion set device is disclosed including a flexible tubing configured to receive an insulin formulation containing at least one phenolic excipient, a base coupled to the tubing and configured to receive the insulin formulation, a catheter coupled to the base and configured to deliver the insulin formulation to a patient, and at least one polymeric sorbent material in fluid communication with the insulin formulation in the device, the at least one polymeric sorbent material being configured to collect the at least one phenolic excipient from the insulin formulation.

According to another embodiment of the present disclosure, an insulin infusion set device is disclosed including a flexible tubing, a base coupled to the tubing, a catheter coupled to the base, a tortuous fluid pathway configured to transport an insulin formulation containing at least one phenolic excipient through the device, and at least one sorbent material positioned along the tortuous fluid pathway, the at least one sorbent material being configured to collect the at least one phenolic excipient from the insulin formulation.

According to yet another embodiment of the present disclosure, an insulin infusion set device is disclosed including a flexible tubing, a base coupled to the tubing a catheter coupled to the base, a fluid pathway configured to transport an insulin formulation containing m-cresol through the device, and at least one polymeric sorbent material positioned along the fluid pathway, the at least one sorbent material being capable of collecting 10% or more of the m-cresol.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein:

FIG. 14 is another schematic cross-sectional view of the device of FIG. 2 applied to a patient's skin, wherein the device includes a medicament on the infusion catheter;

FIG. 15 is another schematic cross-sectional view similar to FIG. 14, wherein the medicament is released into the patient;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
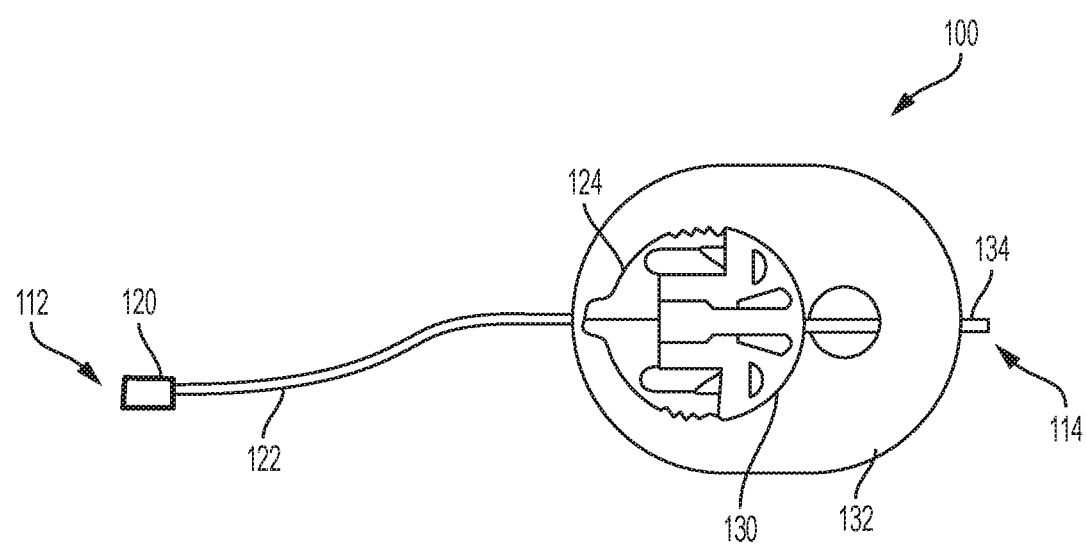
FIG. 1 is a top plan view of a known insulin infusion set (IIS) device.
Figure 2:
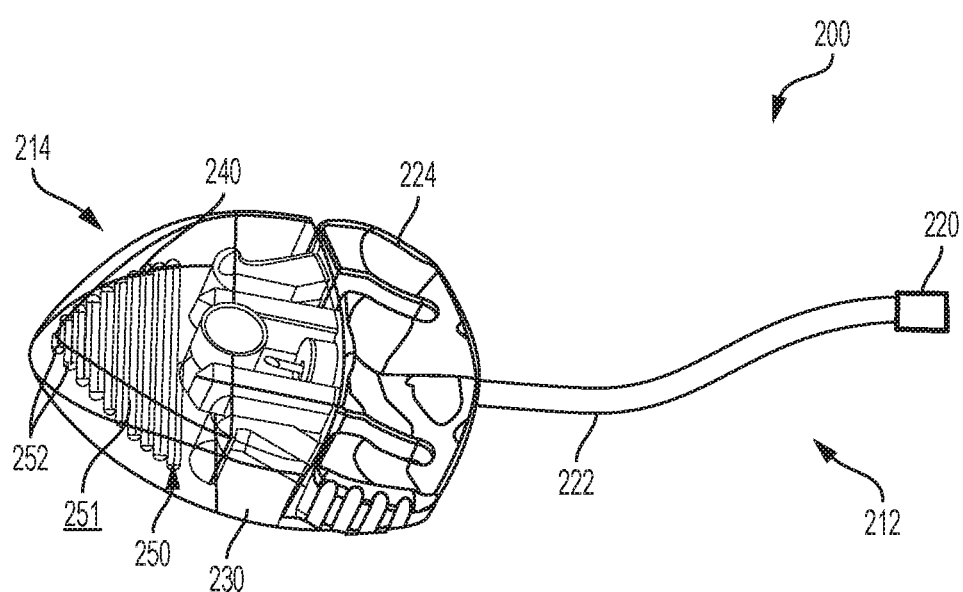
FIG. 2 is a perspective view of an exemplary IIS device of the present disclosure, the device including a reservoir connector, a line set tubing, a base connector, and an infusion base with a tortuous fluid pathway.
Figure 11:
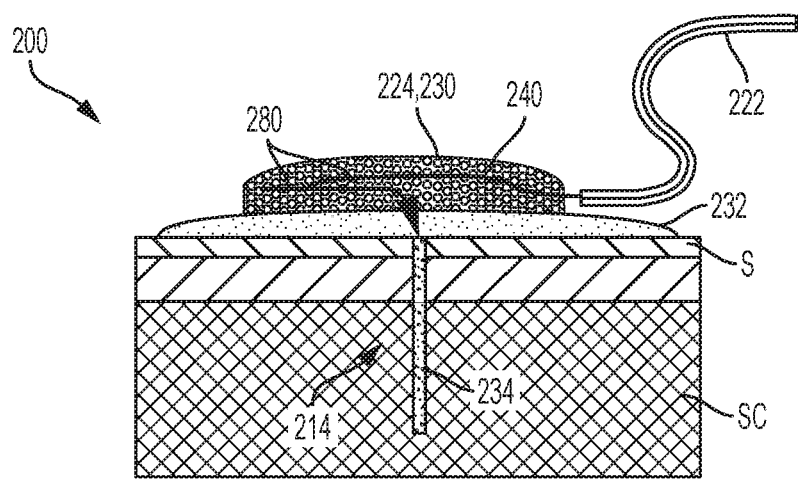
FIG. 11 is a schematic cross-sectional view of the device of FIG. 2 applied to a patient's skin, the device also including an adhesive pad and an infusion catheter, wherein the device contains a bed of microbeads.

An exemplary IIS device 200 of the present disclosure is shown in FIG. 2. Device 200 is similar to device 100 of FIG. 1, with like reference numerals indicating like parts, except as described below. At its first, proximal end 212, device 200 includes a reservoir connector 220 configured to couple with an insulin reservoir (not shown), a flexible line set tubing 222, and a base connector 224 in the shape of a male buckle portion. At its second, distal end 214, device 200 includes an infusion base 230 in the shape of a female buckle portion configured to receive the base connector 224, an adhesive pad 232 (FIG. 11) configured to adhere the infusion base 230 to the patient's skin S (FIG. 11), and an infusion catheter 234 (FIG. 11) configured for insertion into the patient's skin S. In use, the insulin formulation is directed from the pump, through the line set tubing 222, through the infusion catheter 234 (FIG. 11), and into the patient's subcutaneous (SC) tissue (FIG. 11).

Device 200 may include various features designed to achieve longevity in CSII infusion site viability. As a result, the infusion site may last longer than 3 days, 5 days, 7 days, or more, such as about 7 to 14 days, which may reduce insulin waste, reduce scarring, and enable a once-weekly or once-biweekly change-over time frame for a fully integrated artificial pancreas system. These features are described individually below, but it is understood that these features may be used individually or in combination.

While the following disclosure focuses on an IIS platform, the principles described herein have broad applicability in the field of polypeptide delivery, more generally parenteral drug delivery.

1. SORBENT MATERIALS

A first exemplary feature of device 200 includes one or more sorbent materials 240, as shown in FIG. 2. Sorbent material 240 is configured to contact the insulin formulation as it travels through device 200 and collect phenolic excipients (e.g., m-cresol, phenol, methylparaben, ethylparaben, butylbaraben, other preservatives, and combinations thereof) from the insulin formulation by sorption, such as adsorption and/or absorption, prior to delivery to the SC tissue (FIG. 11).

Sorbent material 240 may have a high organic affinity to attract and collect the organic phenolic excipients, in particular m-cresol, by sorption, such as adsorption and/or absorption. Some sorption may occur within a matter of seconds or minutes upon contact. The sorption may increase over time. For example, after a 1-hour exposure time, sorbent material 240 may be capable of collecting over 5%, 10%, 15%, 20%, 25%, or 30% of the m-cresol initially present in the insulation formulation. In certain embodiments, sorbent material 240 may be capable of collecting over 60%, 65%, 70%, 75%, or 80% of the m-cresol after the 1-hour exposure time. The sorption may also increase as the surface area and/or volume of sorbent material 240 increases. Particular examples are provided in Section 4 (Examples 1 and 2) below.

Exemplary sorbent materials 240 include polymers having at least one phenyl ring in the backbone of the polymer structure. In one particular embodiment, sorbent material 240 includes two or more phenyl rings in the backbone of the polymer structure, as shown in Formula (I) below. Examples of such polymer structures based on Formula (I) include aromatic polyurethanes (PU) (e.g., Texin® 285, which is an aromatic polyester-based thermoplastic polyurethane (TPU) available from Covestro AG) and polysulfone.

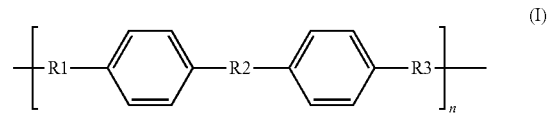

Other exemplary sorbent materials 240 include polymers having at least one phenyl ring in a side chain of the polymer structure, as shown in Formula (II) below. Examples of such polymer structures based on Formula (II) include poly (phenyl methyl siloxane), poly(diphenyl siloxane), and polystyrene.

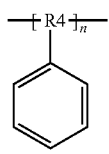

(II)

The above-described polymers may be copolymerized to form a block or random copolymer. For example, the above-described polystyrene may copolymerized to form a poly(styrene-ethylene-butylene-styrene) (SEBS) copolymer (e.g., Mediprene® 500450M available from HEXPOL TPE), or a polystyrene:SEBS block copolymer.

Other exemplary sorbent materials 240 may include nylon 66 (e.g., Technyl® A 205F available: from Solvay Engineering Plastics), ethylene vinyl alcohol (EVOH) (e.g., EVAL™ F171 available from Kuraray Co., Ltd.), polychlorotrifluoroethylene (PCTFE), poly(acrylonitrile) (PAN), poly(vinylidene chloride) (PVDC), polyisoprene, butyl rubber, chlorobutyl rubber, and polypropylene (PP) (e.g., Formolene® 3435E available from Formosa Plastics).

Still other exemplary sorbent materials 240 may include silicone, such as poly(dimethyl siloxane) (PDMS) (e.g., SYLGARD® 184 available from Dow Corning Corporation, MED-6755 available from NuSil Technology, XIAMETER® RSN resins available from Dow Corning Corporation).

The application of sorbent material 240 to device 200 may vary. In certain embodiments, device 200 may be constructed partially or entirely of sorbent material 240. For example, device 200 may be constructed partially or entirely of TPU. In other embodiments, sorbent material 240 may be applied (e.g., coated, lined, over-molded) onto an underlying surface of device 200. For example, a block copolymer comprising styrene and one or more polyolefins (e.g., SEBS) may be applied onto an underlying surface of device 200. In other embodiments, sorbent material 240 may be applied onto a filtration mechanism that is loaded into device 200. Various applications of sorbent material 240 are exemplified below.

The location of sorbent material 240 on device 200 may also vary. In certain embodiments, and as shown in FIG. 2, sorbent material 240 is located at distal end 214 of device 200, more specifically in a fluid pathway 250 that transports the insulin formulation through infusion base 230, such that the insulin formulation contacts sorbent material 240 immediately or soon before delivery to the patient. This arrangement may preserve the integrity and stability of the insulin formulation and minimize risk of insulin precipitation and fluid path occlusion. Additionally or alternatively, sorbent material 240 may be located at distal end 214 of device 200, such as on line set tubing 222 and/or base connector 224 of device 200. In one example, proximal end 212 of device 200 (e.g., line set tubing 222) may include a first sorbent material 240 having a relatively low affinity for phenolic excipients and distal end 214 of device 200 (e.g., infusion base 230) may include a second sorbent material 240 having a relatively high affinity for phenolic excipients, thus creating a diffusion gradient across device 200 that draws the phenolic excipients from the insulin formulation. A diffusion gradient may also be created by co-extruding an element of device 200 (e.g., line set tubing 222) with two different sorbent materials 240 having increasing affinities for phenolic excipients. Various locations of sorbent material 240 are exemplified below.

According to an exemplary embodiment of the present disclosure, device 200 may include one or more modified fluid pathways that transports the insulin formulation through device 200 and is designed to increase the surface area contact, volume contact, and/or the exposure time between the insulin formulation and sorbent material 240. For example, the surface area containing sorbent material 240 may be increased (e.g., elongated) and/or the volume containing sorbent material 240 may be increased (e.g., thickened) relative to a standard fluid pathway, such as by about 5 times, 10 times, 15 times, 20 times, or more. The exposure time between the insulin formulation and sorbent material 240 may have a corresponding increase. Depending on the rate at which the insulin formulation is delivered to the patient, device 200 may be designed to have a total residence time as low as several seconds and as high as several hours. For a patient receiving a basal dose (e.g., 0.75 units/hour), device 200 may be designed to have a total residence time from about 23 minutes to about 10 hours or more, for example. For a patient receiving a bolus dose (e.g., 2 units/hour), device 200 may be designed to have a total residence time from about 8 seconds to about 4 minutes or more, for example. In other embodiments, the fluid pathway may remain unmodified while still achieving sufficient contact with sorbent material 240.

In the illustrated embodiment of FIG. 2, fluid pathway 250 of infusion base 230 is defined by an internal surface 251 having a large surface area to accommodate sorbent material 240. In FIG. 2, this large surface area is achieved by forming a long, indirect, and tortuous fluid pathway 250 through infusion base 230 with a plurality of bends or turns 252 (FIG. 11). It is also within the scope of the present disclosure to achieve this large surface area by placing a plurality of internal obstacles (e.g., fingers) (not shown) on surface 251, for example. Depending on the size and shape of infusion base 230, the number of bends 252 in fluid pathway 250 may vary, such as about 5 bends, 10 bends, 15 bends, 20 bends, or more. The location of each bend 252 may also vary. In FIG. 2, fluid pathway 250 has a zig-zag arrangement with bends 252 located at opposing left and right sides of infusion base 230, but it is also within the scope of the present disclosure for bends 252 to be located at opposing front and rear ends of infusion base 230 and/or at opposing top and bottom surfaces of infusion base 230, for example. The surface 251 that defines the tortuous fluid pathway 250 may have a larger surface area than a standard surface that defines a direct (e.g., linear) pathway, such as about 5 times larger, 10 times larger, 15 times larger, 20 times larger, or more. In this embodiment, the surface 251 defining the illustrative fluid pathway 250 of FIG. 2 may have a total surface area of about 150 mm$^2$ to about 750 mm$^2$. Also, the time required for the insulin formulation to travel through the tortuous fluid pathway 250 may be longer than the time required to travel through a direct (e.g., linear) pathway, such as about 5 times longer, 10 times longer, 15 times longer, 20 times longer, or more. By including sorbent material 240 on surface 251, the insulin formulation traveling through fluid pathway 250 of infusion base 230 may experience increased and/or extended exposure to sorbent material 240 to enhance sorption and removal of phenolic excipients from the insulin formulation.

Figure 3:
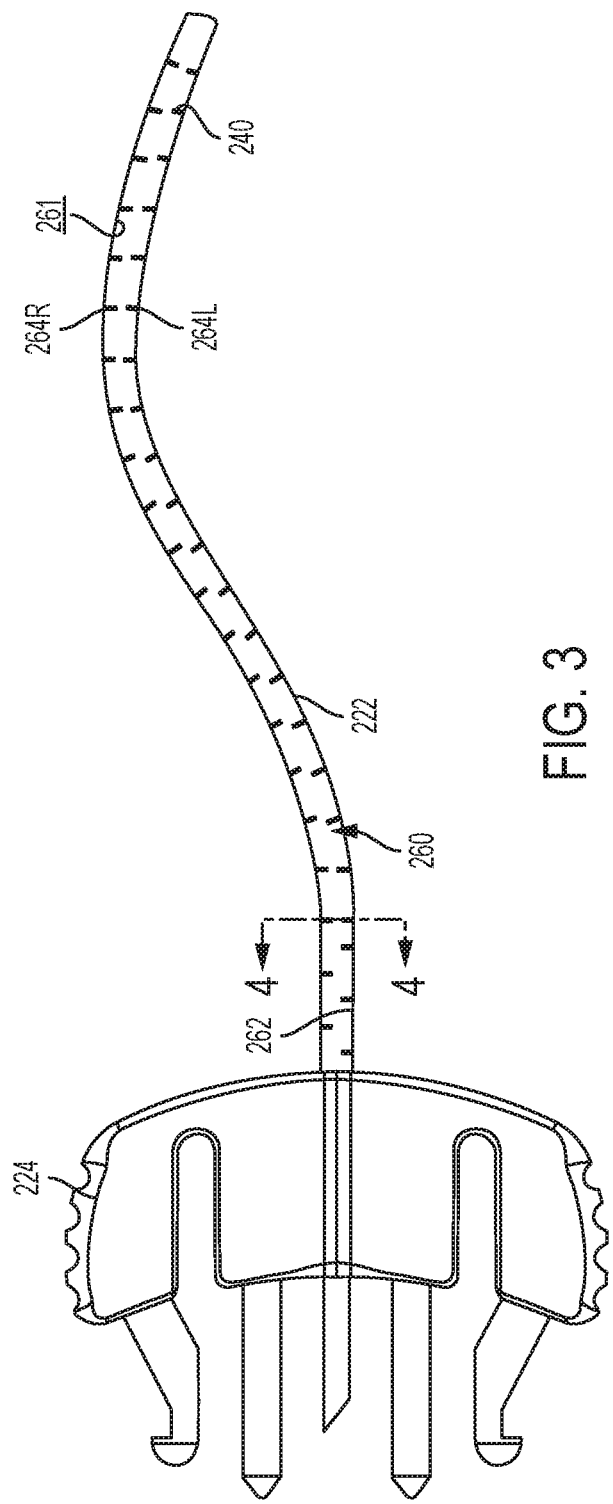
FIG. 3 is a top plan view of the line set tubing and the base connector of FIG. 2.
Figure 4:
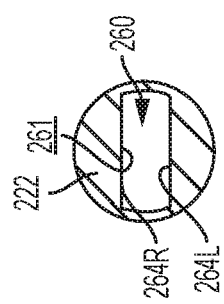
FIG. 4 is a cross-sectional view of the line set tubing of FIG. 3, taken along line 4-4 of FIG. 3.

In the illustrated embodiment of FIGS. 3 and 4, fluid pathway 260 of line set tubing 222 is defined by an internal surface 261 having a large surface area to accommodate sorbent material 240. In FIGS. 3 and 4, this large surface area is achieved by placing a plurality of internal obstacles, specifically left-side fingers 264L and right-side fingers 264R, on surface 261. In this embodiment, the surface 261 (including fingers 264L, 264R) defining the illustrative fluid pathway 260 of FIGS. 3 and 4 may have a total surface area of about 0.6 inches$^2$ to about 2 inches$^2$. Opposing pairs of fingers 264L, 264R may be longitudinally offset from each other, as shown near base connector 224, which may create a tortuous fluid pathway 260 with bends or turns 262. Additionally or alternatively, opposing pairs of fingers 264L, 264R may be longitudinally aligned with each other, as shown in FIG. 4, which may create non-circular areas of narrow cross-section in fluid pathway 260 (e.g., in areas with fingers 264L, 264R) and areas of wide cross-section in fluid pathway 260 (e.g., in areas without any fingers 264L, 264R). By including sorbent material 240 on fingers 264L, 264R and/or the rest of surface 261, the insulin formulation traveling through fluid pathway 260 of line set tubing 222 may experience increased and/or extended exposure to sorbent material 240 to enhance sorption and removal of phenolic excipients from the insulin formulation.

Figure 5:
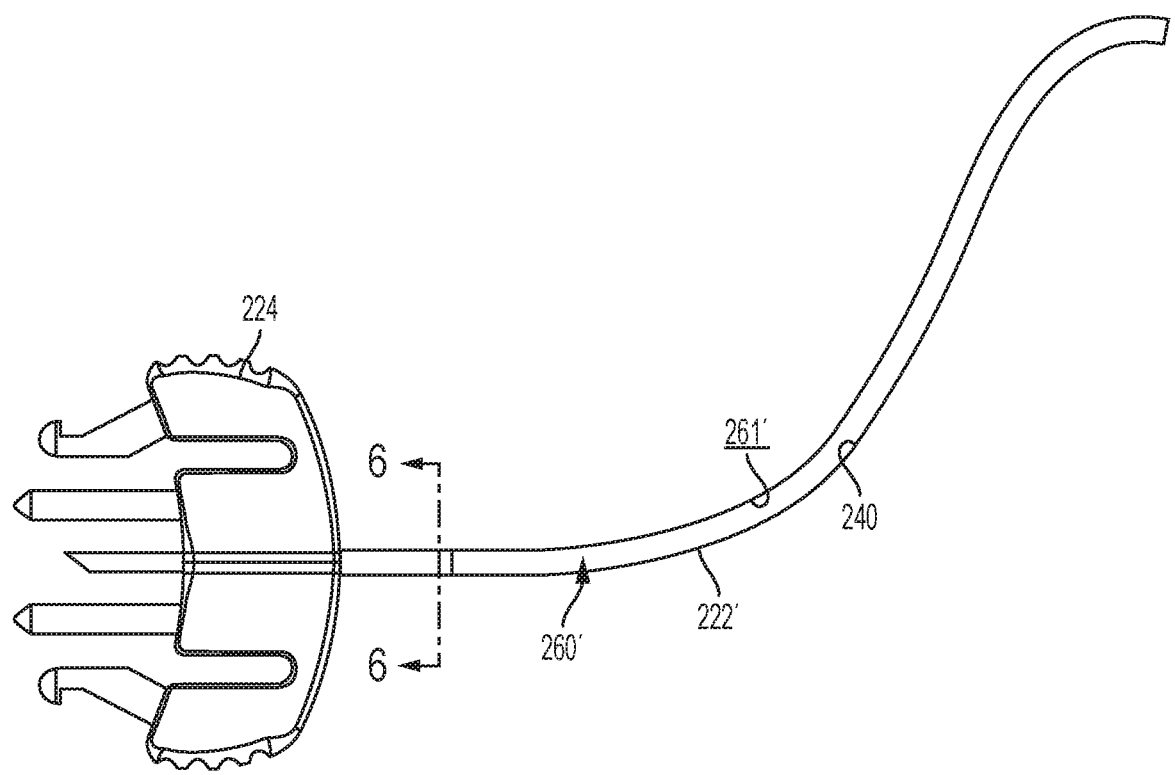
FIG. 5 is a top plan view of a second line set tubing with the base connector of FIG. 2.
Figure 6:
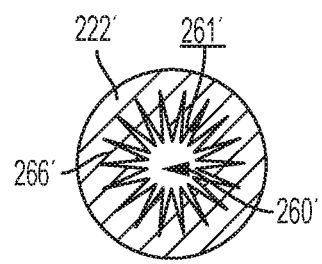
FIG. 6 is a cross-sectional view of the second line set tubing of FIG. 5; taken along line 6-6 of FIG. 5.

In the illustrated embodiment of FIGS. 5 and 6, fluid pathway 260' of line set tubing 222' is defined by an internal surface 261' having a large surface area to accommodate sorbent material 240. In FIG. 6, this large surface area is achieved by placing a plurality of internal extensions, specifically triangular-shaped fingers 266', around surface 261' to form a non-circular, star-shaped fluid pathway 260'. In this embodiment, the surface 261' (including fingers 266') defining the illustrative fluid pathway 260' of FIGS. 5 and 6 may have a total surface area of about 7 inches$^2$ to about 15 inches$^2$. Each finger 266' may extend the entire length of line set tubing 222', or discrete fingers 266' may be positioned along the length of line set tubing 222'. It is also within the scope of the present disclosure for each finger 266' to follow a spiral path across line set tubing 222' such that pathway 260' also follows a spiral path. By including sorbent material 240 on fingers 266' and/or the rest of surface 261', the insulin formulation traveling through fluid pathway 260' of line set tubing 222' may experience increased and/or extended exposure to sorbent material 240 to enhance sorption and removal of phenolic excipients from the insulin formulation.

Figure 7:
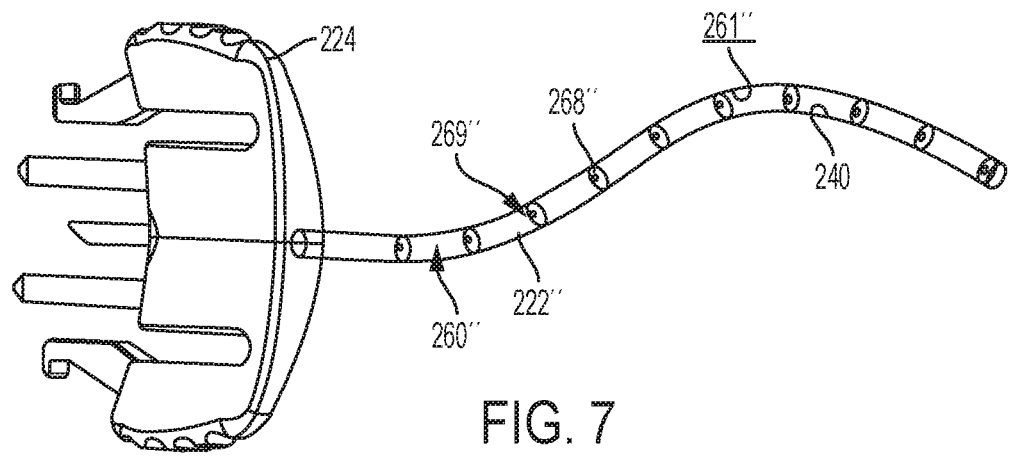
FIG. 7 is a top plan view of a third line set tubing with the base connector of FIG. 2.
Figure 8:
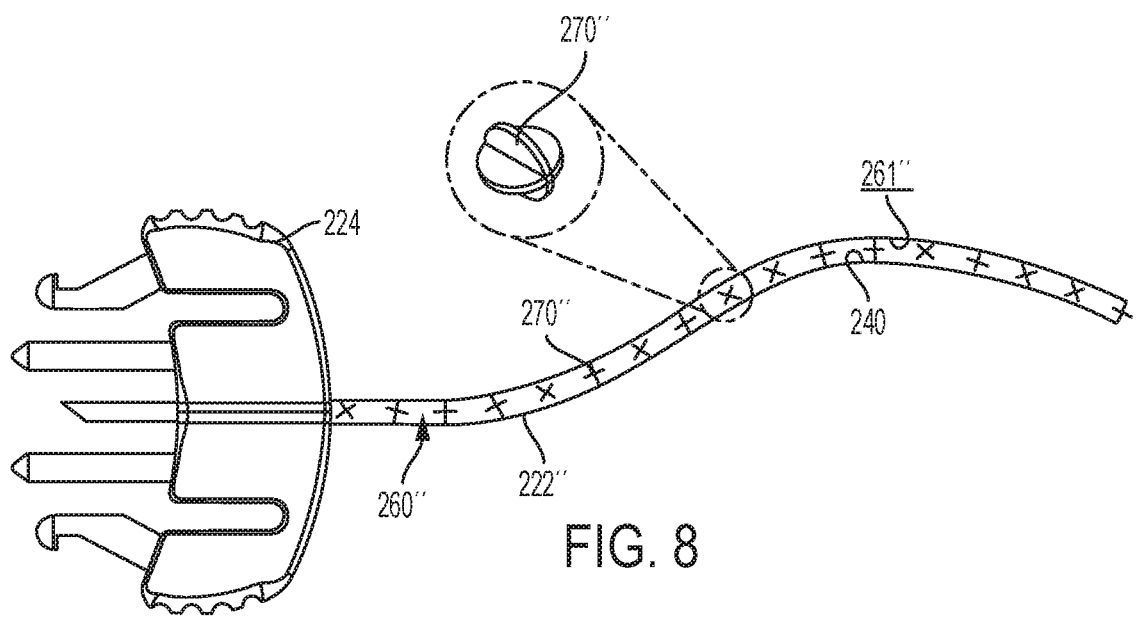
FIG. 8 is a top plan view of a fourth line set tubing with the base connector of FIG. 2.

In the illustrated embodiments of FIGS. 7 and 8, fluid pathway 260" of line set tubing 222" is defined by an internal surface 261" having a large surface area to accommodate sorbent material 240. In FIG. 7, this large surface area is achieved by placing a plurality of internal obstacles, specifically circular-shaped discs 268" with holes 269", in fluid pathway 260". In this embodiment, the surface 261" (including discs 268") defining the illustrative fluid pathway 260" of FIG. 7 may have a total surface area of about 0.6 inches$^2$ to about 2 inches$^2$. The holes 269" of adjacent discs 268" may be positioned out of alignment with each other to enhance the tortuous nature of fluid pathway 260". In FIG. 8, this large surface area is achieved by placing a plurality of internal star-shaped paddles 270", in fluid pathway 260". In this embodiment, the surface 261" (including paddles 270") defining the illustrative fluid pathway 260" of FIG. 8 may have a total surface area of about 0.6 inches$^2$ to about 2 inches$^2$. Adjacent paddles 270" may be positioned out of alignment with each other to enhance the tortuous nature of fluid pathway 260". By including sorbent material 240 on discs 268", paddles 270", and/or the rest of each surface 261", the insulin formulation traveling through fluid pathway 260" of line set tubing 222" may experience increased and/or extended exposure to sorbent material 240 to enhance sorption and removal of phenolic excipients from the insulin formulation.

Figure 9:
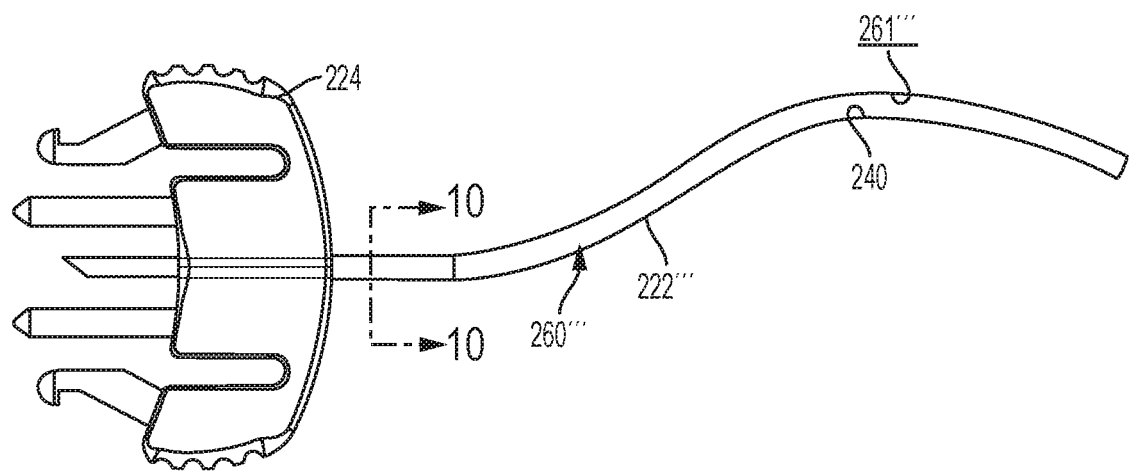
FIG. 9 is a top plan view of a fifth line set tubing with the base connector of FIG. 2.
Figure 10:
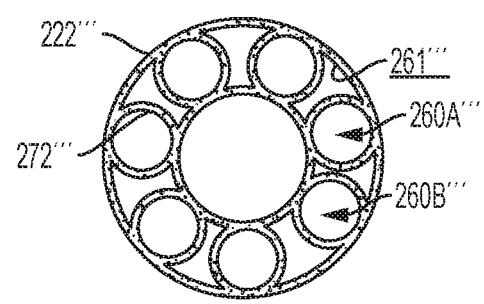
FIG. 10 is a cross-sectional view of the fifth line set tubing of FIG. 9, taken along line 10-10 of FIG. 9.

In the illustrated embodiment of FIGS. 9 and 10, fluid pathway 260''' of line set tubing 222''' is defined by an internal surface 261''' having a large surface area to accommodate sorbent material 240. In FIG. 10, this large surface area is achieved by placing a plurality of internal walls, specifically circular-shaped walls 272''', in line set tubing 222''' to divide fluid pathway 260''' into a plurality of individual fluid pathways 260A''', 260B''', etc. In this embodiment, the surface 261''' (including walls 272''') defining the illustrative fluid pathway 260''' of FIGS. 9 and 10 may have a total surface area of about 1.3 inches$^2$ to about 4.6 inches$^2$. In one embodiment, the insulin formulation may travel through a single fluid pathway (e.g., fluid pathway 260A''') in close proximity to the surrounding circular-shaped wall 272'''. In another embodiment, the fluid pathways may be interconnected at the ends of line set tubing 222''' such that the insulin formulation travels back and forth through a plurality of interconnected fluid pathways (e.g., fluid pathways 260A''', 260B''', etc.) in a zig-zag arrangement. By including sorbent material 240 on internal walls 272''' and/or the rest of surface 261''', the insulin formulation traveling through line set tubing 222''' may experience increased and/or extended exposure to sorbent material 240 to enhance sorption and removal of phenolic excipients from the insulin formulation.

In another embodiment, device 200 may include an enlarged fluid well (not shown) configured to hold the insulin formulation for an extended period of time. The well may be located along a fluid pathway of line set tubing 222, base connector 224, and/or infusion base 230 of device 200, for example. The surface that defines the well may include sorbent material 240, as discussed above.

According to another exemplary embodiment of the present disclosure, device 200 may include one or more filtration mechanisms of sorbent material 240 configured to increase the surface area contact, volume contact, and/or the exposure time between the insulin formulation and sorbent material 240. The filtration mechanism may be located along a fluid pathway of line set tubing 222, base connector 224, and/or infusion base 230 of device 200, for example. In other embodiments, device 200 may lack the filtration mechanism while still achieving sufficient contact with sorbent material 240.

In the illustrated embodiment of FIG. 11 base connector 224 and/or infusion base 230 includes a bed of microbeads 280. By including sorbent material 240 on microbeads 280 themselves and/or the internal walls of device 200, the insulin formulation traveling through microbeads 280 may experience increased and/or extended exposure to sorbent material 240 to enhance sorption and removal of phenolic excipients from the insulin formulation.

Figure 12:
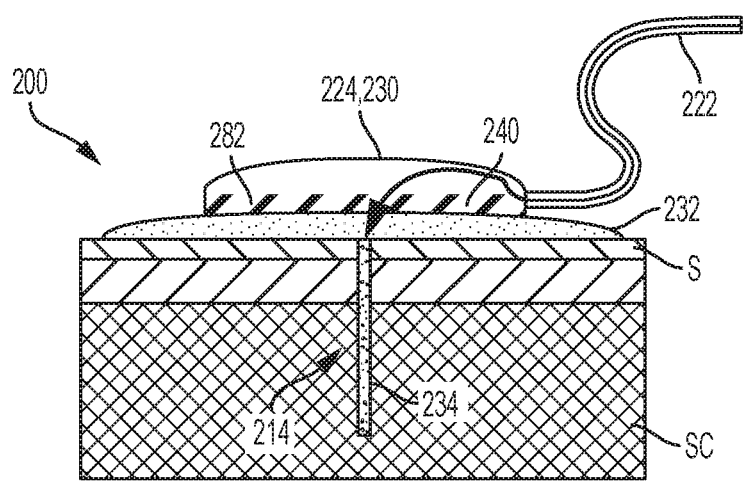
FIG. 12 is another schematic cross-sectional view similar to FIG. 11, wherein the device contains a porous filtration membrane.

In the illustrated embodiment of FIG. 12, base connector 224 and/or infusion base 230 includes a porous filtration membrane 282. The membrane 282 may be fibrous in nature and may be woven or non-woven. By including sorbent material 240 on membrane 282 itself and/or the internal walls of device 200, the insulin formulation traveling through membrane 282 may experience increased and/or extended exposure to sorbent material 240 to enhance sorption and removal of phenolic excipients from the insulin formulation.

Figure 13:
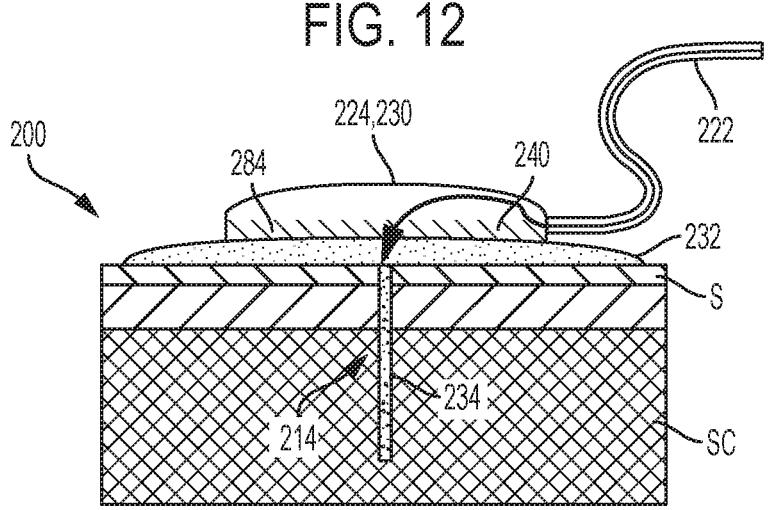
FIG. 13 is another schematic cross-sectional view similar to FIG. 11, wherein the device contains a bed of microfibers.

In the illustrated embodiment of FIG. 13, base connector 224 and/or infusion base 230 of device 200 includes a bed of microfibers 284. By including sorbent material 240 on microfibers 284 themselves and/or the internal walls of device 200, the insulin formulation traveling through microfibers 284 may experience increased and/or extended exposure to sorbent material 240 to enhance sorption and removal of phenolic excipients from the insulin formulation.

2. MEDICAMENTS

Figures 14, 15:
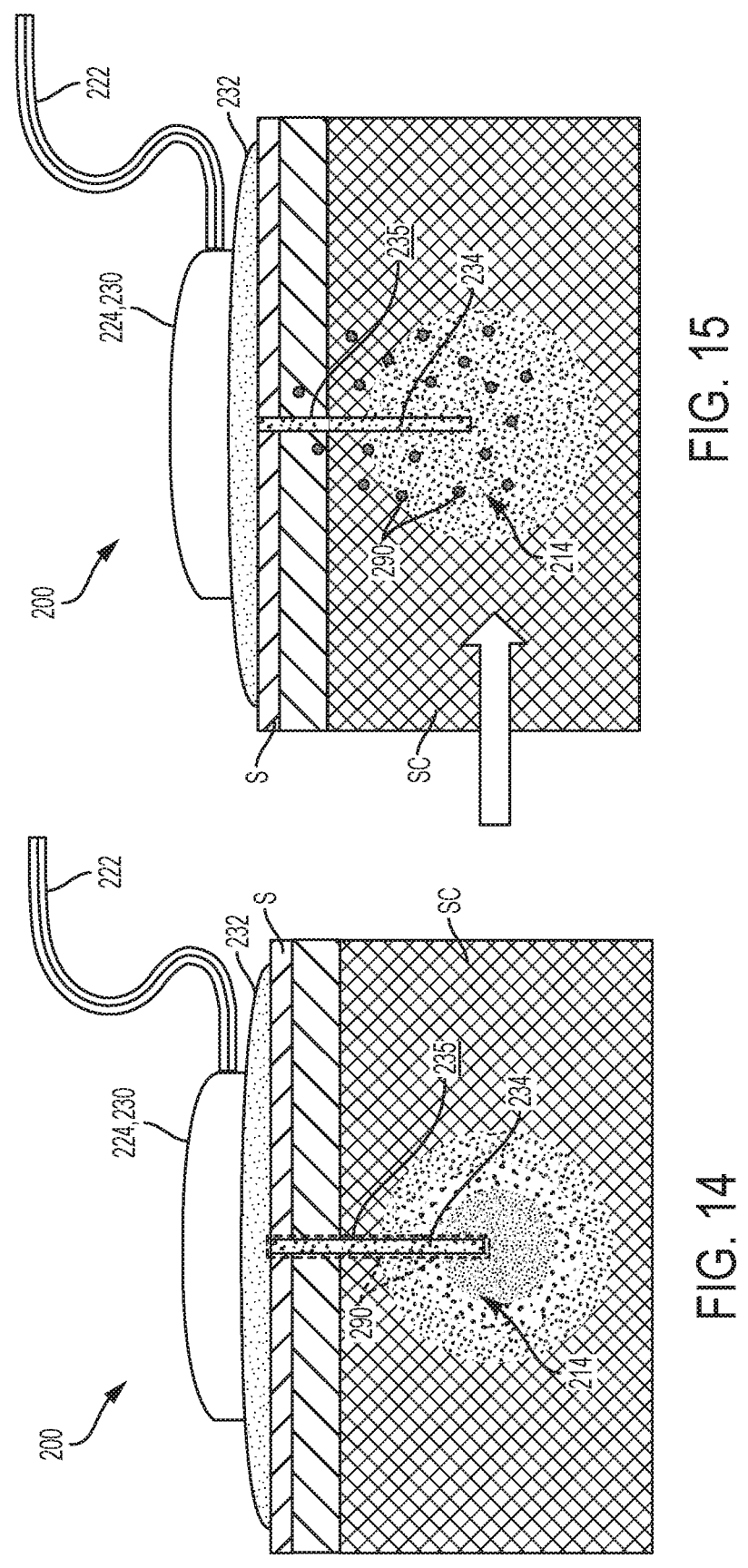

A second exemplary feature of device 200 includes a medicament 290, as shown in FIG. 14, configured to reduce inflammation or slow the progression of the inflammatory response. Medicament 290 may be located along the fluid pathway of device 200 and configured for release and dissolution into the insulin formulation traveling through device 200 for delivery to the patient.

Medicament 290 may include one or more anti-inflammatory agents. Exemplary anti-inflammatory agents include ibuprofen, naproxen, aspirin, plumbagin, plumericin, celecoxib, diclofenac, etodolac, indomethacin, ketoprofen, ketorolac, nabumetone, oxaprozin, piroxicam, salsalate, sulindac, tolmetin, rapamycin, dexamethasone, betamethasone, heparin, sirolimus, and paxlitaxel, for example.

Medicament 290 may also include other therapeutic agents alone or in combination with the anti-inflammatory agents. Exemplary therapeutic agents include inhibitors of tyrosine kinase (e.g., masitinib), inhibitors of the matricellular protein Thrombospondin 2 (TSP2), inhibitors of fibrosis-stimulating cytokines including Connective Tissue Growth Factor (CTGF), inhibitors of members of the integrin family of receptors, Vascular Endothelial Growth Factor (VEGF), antimicrobial agents (e.g., silver) and diffusion enhancing agents (e.g., hyaluronidase), for example. In one particular example, medicament 290 includes the therapeutic agent VEGF in combination with the anti-inflammatory agent dexamethasone, but other combinations are also contemplated.

Medicament 290 may be combined with one or more polymers to form a blend or matrix, which may improve film or coating properties, improve solubility or elution properties, and/or impart a time-release effect to elution of medicament 290 into the patient's SC tissue. Exemplary polymers include polyethylene glycol (PEG), polyvinyl alcohol (PVA), polylactic acid (PLA), polyglycolic acid (PGA), poly(lactic-co-glycolic acid) (PLGA), polyhydroxyethylmethacrylate (PHEMA), poly(methacrylic acid) (PMAA), alginate, (poly) phosphoryl chlorines and (poly) ester amides, for example.

The application of medicament 290 to device 200 may vary. In certain embodiments, medicament 290 may be incorporated (e.g., embedded) directly into device 200. In other embodiments, medicament 290 may be applied (e.g., coated) onto an underlying surface of device 200. In other embodiments, medicament 290 may be applied onto a filtration mechanism that is loaded into device 200.

The location of medicament 290 on device 200 may also vary. As noted above, medicament 290 may be located along the fluid pathway of device 200. More specifically, medicament 290 may be located inside line set tubing 222, inside base connector 224, inside infusion base 230, inside infusion catheter 234, and/or outside infusion catheter 234 of device 200. In the illustrated embodiment of FIG. 14, for example, medicament 290 is coated onto an outer surface 235 of infusion catheter 234 to substantially cover the outer surface 235. In FIG. 15, medicament 290 disperses into the patient's SC tissue along with the insulin formulation traveling through device 200, which may reduce the magnitude or velocity of the patient's inflammatory response.

3. DISPERSIVE CATHETER

Figure 16:
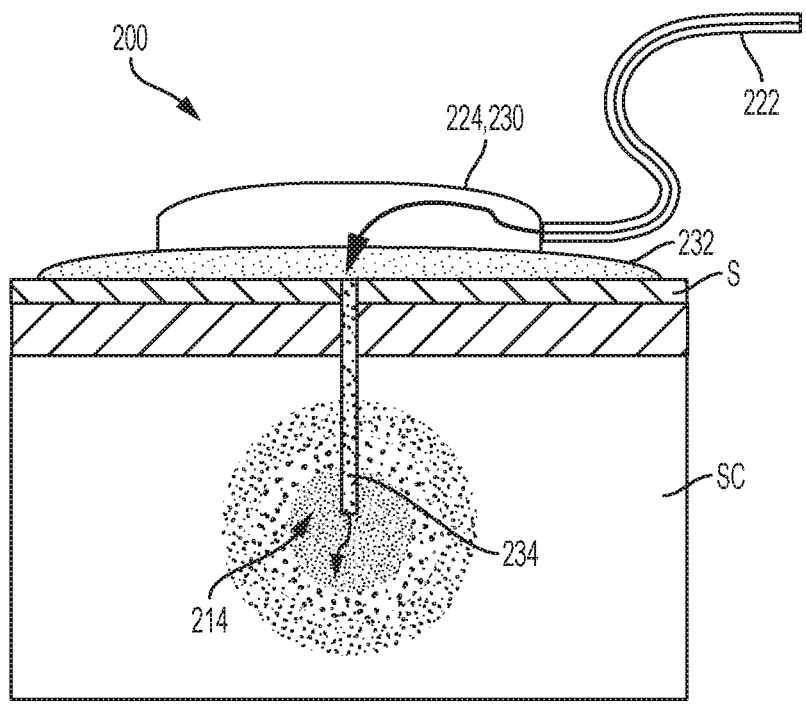
FIG. 16 is another schematic cross-sectional view of the device of FIG. 2 applied to a patient's skin, wherein the infusion catheter includes a single delivery aperture.
Figure 17:
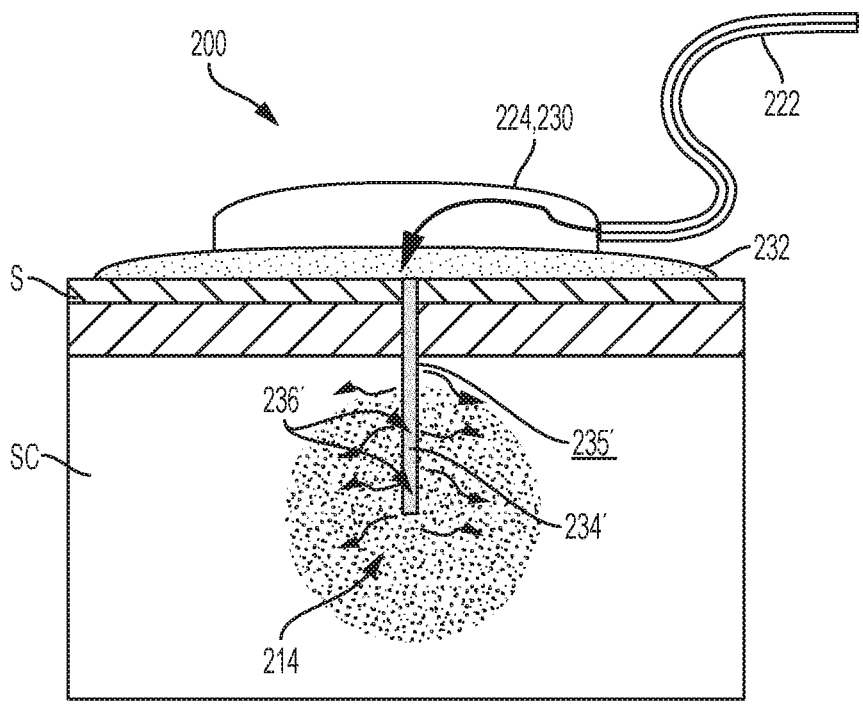
FIG. 17 is another schematic cross-sectional view similar to FIG. 16, wherein the infusion catheter includes a plurality of delivery apertures.

A third exemplary feature of device 200 includes a dispersive infusion catheter 234', as shown in FIG. 17. The dispersive infusion catheter 234' may be designed to deliver the insulin formulation (and any phenolic excipients and/or medicaments 290 dissolved therein) in a more diffuse manner over a greater volume, thereby distributing the SC tissue insult over a greater volume and minimizing localized impact. For example, rather than exiting infusion catheter 234 at a single location (e.g., at the distal-most tip 214), as shown in FIG. 16, the insulin formulation may exit the dispersive infusion catheter 234' through a plurality of apertures 236' distributed across outer surface 235', as shown in FIG. 17. The dispersive infusion catheter 234' of FIG. 17 may have a sponge-like construction with a plurality of distinct or interconnected internal passageways (not shown) leading to the plurality of apertures 236'.

4. EXAMPLES

Example 1: Sorption of m-Cresol with SEBS

A plurality of samples were prepared, each sample including a sorbent material immersed in an insulin formulation. Each sorbent material was a molded Mediprene® 500450M SEBS structure having a surface area of 450 mm$^2$ and a volume of 375 mm$^3$, resulting in a 1.2 mm$^{-1}$ ratio of surface area to volume. Each insulin formulation was a 1 mL Humalog® U-100 insulin lispro formulation, which is available from Eli Lilly and Company. After a predetermined soak time of 2 minutes, 4 minutes, 15 minutes, 25 minutes, 60 minutes, 90 minutes, 180 minutes, 6 hours, 9 hours, 12 hours, 24 hours, 2 days, 4 days, 6 days, 8 days, or 10 days (240 hours), the SEBS sorbent material was removed from its insulin formulation. Then, the m-cresol concentration of each insulin formulation was measured using reverse phase High Performance Liquid Chromatography (HPLC).

Figure 18:
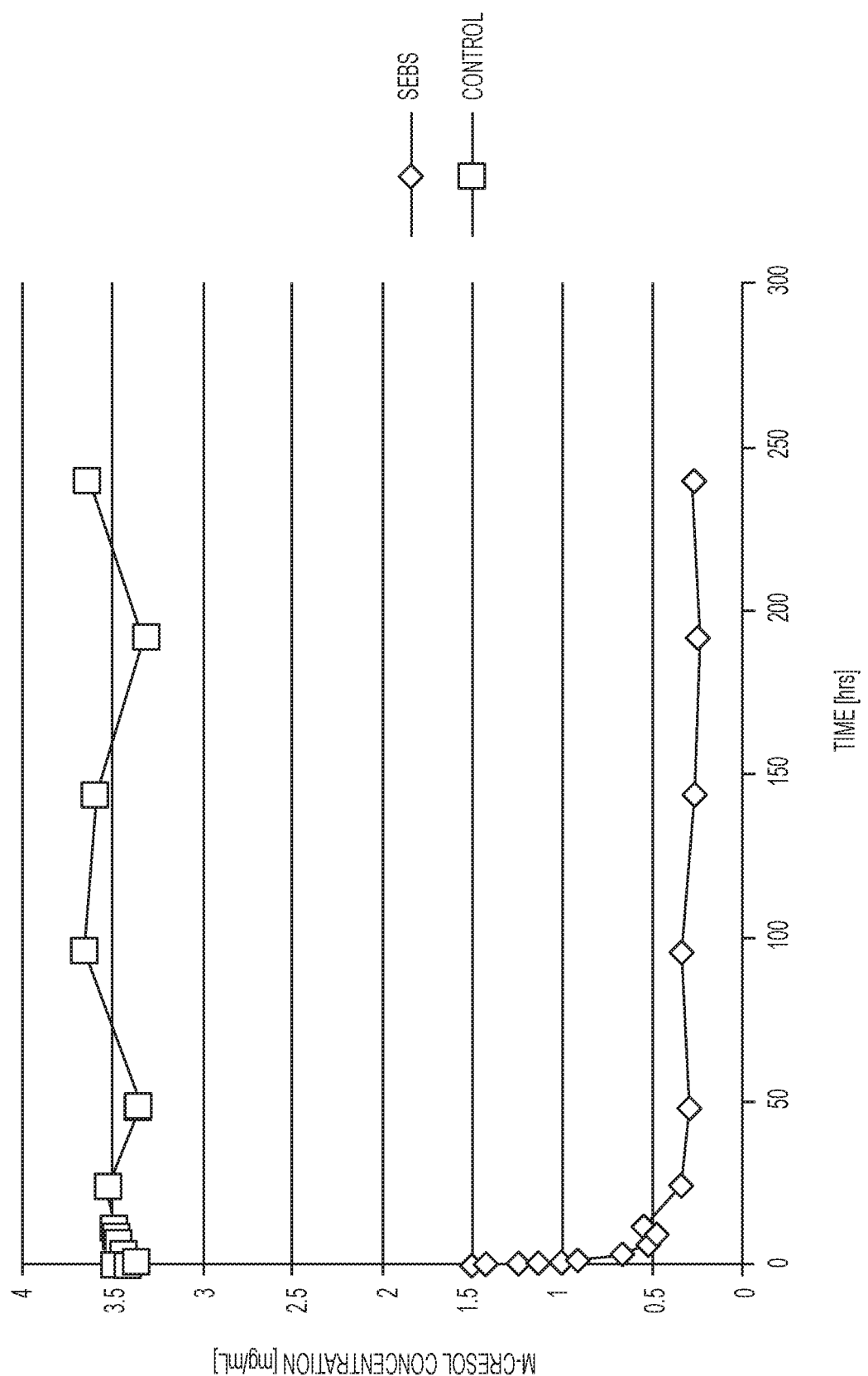
FIG. 18 is a chart showing m-cresol sorption over time when an insulin formulation is exposed to a first sorbent material.

The results are presented in FIG. 18, which shows that the m-cresol concentration in the insulin formulation decreased over time when exposed to the SEBS sorbent material compared to a control sample. After 1 hour, the m-cresol concentration had decreased from about 3.4 mg/mL to about 0.9 mg/mL, which represents a 74% decrease. After 240 hours, the m-cresol concentration had decreased to about 0.3 mg/mL, which represents a 91% overall decrease.

Additional samples of the SEBS sorbent material were prepared and tested in a similar manner. The sorption results were impacted by both surface area and volume of the SEBS sorbent material, which suggests that m-cresol may be collected through both surface adsorption and bulk absorption. For example, two of the additional samples had smaller surfaces areas than the above samples, specifically 82 mm$^2$ and 165 mm$^2$. After 1 hour, these smaller samples had collected less m-cresol than the larger samples above, specifically 19% sorption for the 82 mm$^2$ size sample and 34% sorption for the 165 mm$^2$ sample.

Example 2: Sorption of m-Cresol with TPU

Figure 19:
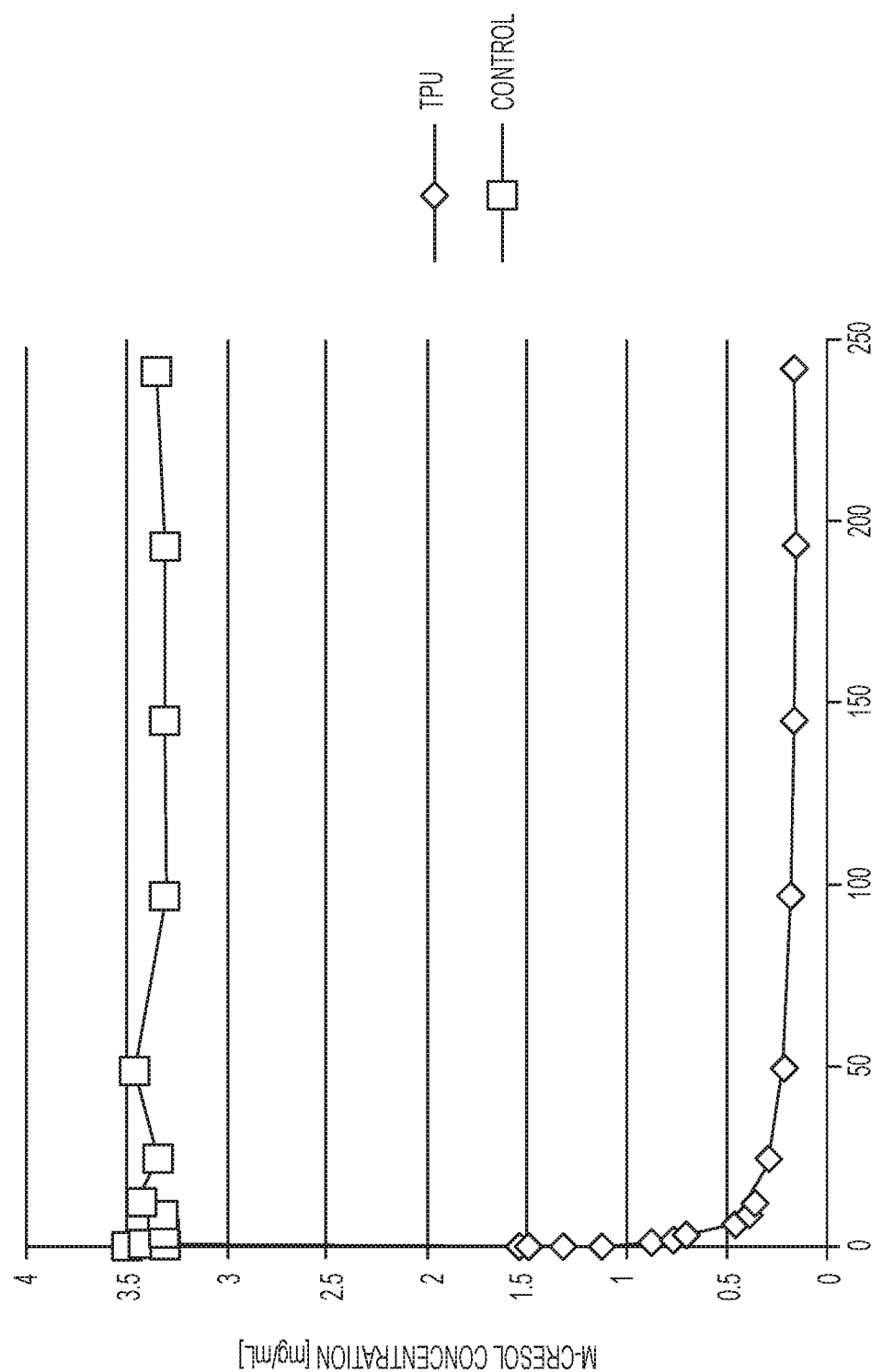
FIG. 19 is a chart showing m-cresol sorption over time when the insulin formulation is exposed to a second sorbent material.

Example 1 was repeated, but with Texin® 285 TPU as the sorbent material. The results are presented in FIG. 19, which shows that the m-cresol concentration in the insulin formulation decreased over time when exposed to the TPU sorbent material compared to a control sample. After 1 hour, the m-cresol concentration had decreased from about 3.3 mg/mL to about 0.9 mg/mL, which represents a 73% decrease. After 240 hours, the m-cresol concentration had decreased to about 0.1 mg/mL, which represents a 97% decrease.

Additional samples of the TPU sorbent material were prepared and tested in a similar manner. The sorption results were impacted by both surface area and volume of the SEBS sorbent material, which suggests that m-cresol may be collected through both surface adsorption and bulk absorption. For example, one of the additional samples had a smaller surface area than the above samples, specifically 150 mm². After 1 hour, this smaller sample had collected less m-cresol than the larger samples above, specifically 29% sorption.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which tall within the limits of the appended claims.

What is claimed is:

1. An insulin infusion set device comprising:
    a flexible tubing configured to receive an insulin formulation containing at least one phenolic excipient;
    a base coupled to the tubing and configured to receive the insulin formulation;
    a catheter coupled to the base and configured to deliver the insulin formulation to a patient;
    a tortuous fluid pathway positioned in the base and configured to transport the insulin formulation through the base, the tortuous fluid pathway including a plurality of bends; and
    at least one polymeric sorbent material positioned along the tortuous fluid pathway and in fluid communication with the insulin formulation in the device, the at least one polymeric sorbent material being configured to collect the at least one phenolic excipient from the insulin formulation by sorption.

2. The device of claim 1, wherein the at least one phenolic excipient is m-cresol, and the at least one polymeric sorbent material is capable of collecting 10% or more of the m-cresol.

3. The device of claim 1, wherein the at least one polymeric sorbent material has at least one phenyl ring in a backbone of the polymer.

4. The device of claim 3, wherein the at least one polymeric sorbent material is an aromatic polyester-based thermoplastic polyurethane (TPU).

5. The device of claim 1, wherein the at least one polymeric sorbent material has at least one phenyl ring in a side chain of the polymer.

6. The device of claim 5, wherein the at least one polymeric sorbent material is a poly(styrene-ethylene-butylene-styrene) (SEBS) copolymer.

7. The device of claim 1, wherein the at least one polymeric sorbent material is located at a distal end of the device such that the at least one phenolic excipient is collected before the insulin formulation is delivered to the patient.

8. The device of claim 1, wherein the tortuous fluid pathway of the device has a zig-zag arrangement.

9. The device of claim 1, wherein the tubing is constructed of or coated with the at least one polymeric sorbent material.

10. The device of claim 1, wherein the base is constructed of or coated with the at least one polymeric sorbent material.

11. The device of claim 1, wherein the at least one polymeric sorbent material is located on at least one of the group consisting of: a bed of microbeads, a porous filtration membrane, and a bed of microfibers.

12. The device of claim 1, further comprising a medicament comprising at least one anti-inflammatory agent coupled to the device in fluid communication with the insulin formulation.

13. The device of claim 1, wherein an outer surface of the catheter includes a plurality of apertures configured to deliver the insulin formulation to the patient in a diffuse manner.

14. An insulin infusion set device comprising:
    a flexible tubing;
    a base coupled to the tubing;
    a catheter coupled to the base;
    a tortuous fluid pathway configured to transport an insulin formulation containing at least one phenolic excipient through the device; and
    a first sorbent material having a relatively lower affinity for phenolic excipients and a second sorbent material having a relatively higher affinity for phenolic excipients, the first and second sorbent materials both positioned along at least the tortuous fluid pathway to provide a diffusion gradient across the device, the first and second sorbent materials being configured to collect the at least one phenolic excipient from the insulin formulation by sorption.

15. The device of claim 14, wherein at least one of the first and second sorbent materials is a polymer.

16. The device of claim 15, wherein at least one of the first and second sorbent materials is an aromatic polyester-based thermoplastic polyurethane (TPU) or a poly(styrene-ethylene-butylene-styrene) (SEB S) copolymer.

17. The device of claim 14, wherein at least a portion of the tortuous fluid pathway is located in the tubing and defined by a plurality of internal obstacles in the tubing.

18. The device of claim 14, wherein at least a portion of the tortuous fluid pathway is located in the base and includes a plurality of bends to form a zig-zag arrangement.

19. An insulin infusion set device comprising:
    a flexible tubing comprising a tortuous fluid pathway, the tortuous fluid pathway including a plurality of fluid pathways interconnected at ends of the plurality of fluid pathways and configured in a zig-zag arrangement;
    a base coupled to the tubing;
    a catheter coupled to the base;
    the fluid pathways configured to transport an insulin formulation containing m-cresol through the device; and
    at least one polymeric sorbent material positioned along the plurality of fluid pathways, the at least one polymeric sorbent material being capable of collecting 10% or more of the m-cresol by sorption.

20. The device of claim 19, wherein a surface that defines the tortuous fluid pathway is constructed of or coated with the at least one polymeric sorbent material.

21. The device of claim 19, wherein the at least one polymeric sorbent material is selected from the group consisting of: aromatic polyester-based thermoplastic polyurethane, polysulfone, poly(phenyl methyl siloxane), poly(diphenyl siloxane), polystyrene, poly(styrene-ethylene-butylene-styrene), nylon 66, ethylene vinyl alcohol, polychlorotrifluoroethylene, poly(acrylonitrile), poly(vinylidene chloride), polyisoprene, butyl rubber, chlorobutyl rubber, polypropylene (PP), and silicone.

22. The device of claim 14, wherein the device includes a proximal end and a distal end and the proximal end includes the first sorbent material and the distal end includes the second sorbent material.

\* \* \* \* \*

UNITED STATES PATENT AND TRADEMARK OFFICE
CERTIFICATE OF CORRECTION

Page 1 of 1

PATENT NO. : 11,045,601 B2
APPLICATION NO. : 16/094628
DATED : June 29, 2021
INVENTOR(S) : Christopher John Demaria et al.

It is certified that error appears in the above-identified patent and that said Letters Patent is hereby corrected as shown below:

In the Claims

Column 12 Line 40: In Claim 16, delete "(SEB S)" and insert -- (SEBS) --, therefor.

Signed and Sealed this
Eleventh Day of January, 2022

Drew Hirshfeld
*Performing the Functions and Duties of the
Under Secretary of Commerce for Intellectual Property and
Director of the United States Patent and Trademark Office*